United States Patent
Wang et al.

(10) Patent No.: US 9,714,235 B2
(45) Date of Patent: Jul. 25, 2017

(54) QUINAZOLINE DERIVATIVES, COMPOSITIONS THEREOF, AND USE AS PHARMACEUTICALS

(71) Applicant: Shanghai Fochon Pharmaceutical Co., Ltd., Shanghai (CN)

(72) Inventors: Weibo Wang, Moraga, CA (US); Xingdong Zhao, Moraga, CA (US); Tongshuang Li, Surrey (CA); Qiang Tian, Chongqing (CN); Ling Chen, Chongqing (CN); Zuwen Zhou, Chongqing (CN); Zhifu Li, Chongqing (CN); Xianlong Wang, Chongqing (CN); Yue Rong, Chongqing (CN); Lihua Jiang, Chongqing (CN); Yanxin Liu, Chongqing (CN); Jing Sun, Chongqing (CN); Fanxin Zeng, Chongqing (CN)

(73) Assignee: Shanghai Fochon Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/905,619

(22) PCT Filed: Jul. 17, 2014

(86) PCT No.: PCT/CN2014/082377
§ 371 (c)(1),
(2) Date: Jan. 15, 2016

(87) PCT Pub. No.: WO2015/007219
PCT Pub. Date: Jan. 22, 2015

(65) Prior Publication Data
US 2016/0168129 A1    Jun. 16, 2016

Related U.S. Application Data

(60) Provisional application No. 61/856,005, filed on Jul. 18, 2013.

(51) Int. Cl.
*C07D 403/12* (2006.01)
*C07D 405/14* (2006.01)
*A61K 45/06* (2006.01)
*A61K 31/517* (2006.01)

(52) U.S. Cl.
CPC .......... *C07D 403/12* (2013.01); *A61K 31/517* (2013.01); *A61K 45/06* (2013.01); *C07D 405/14* (2013.01)

(58) Field of Classification Search
None
See application file for complete search history.

(56) References Cited

U.S. PATENT DOCUMENTS

2014/0161801 A1    6/2014    Wu et al.
2016/0083376 A1    3/2016    Wang et al.

FOREIGN PATENT DOCUMENTS

WO    WO 2012159457    * 11/2012
WO    WO 2013131424    *  9/2013

OTHER PUBLICATIONS

International Search Report for International Application No. PCT/CN2014/082377 dated Sep. 16, 2014.
Lynch et al. "Efficient asymmetric synthesis of ABT-594; a potent, orally effective analgesic," Tetrahedron: Asymmetry 1998, vol. 9, Issue 16, Aug. 1998, pp. 2791-2794, Elsevier Science Ltd. doi:10.1016/S0957-4166(98)00291-2.
Rewcastle et al. "Tyrosine Kinase Inhibitors. 9. Synthesis and Evaluation of Fused Tricyclinc Quinazoline Analogues as ATP Site Inhibitors of the Tyrosine Kinase Activity of the Epidermal Growth Fcator Receptor," Journal of Medicinal Chemistry, 1996, vol. 39, Issue 4, p. 918-928.
Evans et al. "Azetidine Based Transition State Analogue Inhibitors of N-Ribosyl Hydrolases and Phosphorylases," Journal of Medicinal Chemistry, 2008, vol. 51, Issue 4, pp. 948-956, DOI: 10.1021/jm701265n.

* cited by examiner

*Primary Examiner* — Paul V Ward
(74) *Attorney, Agent, or Firm* — Jenkins, Wilson, Taylor & Hunt

(57) ABSTRACT

Disclosed herein are protein kinase inhibitors, more particularly novel quinazoline derivatives and pharmaceutical compositions thereof, and method of use thereof.

2 Claims, 1 Drawing Sheet

QUINAZOLINE DERIVATIVES, COMPOSITIONS THEREOF, AND USE AS PHARMACEUTICALS

CROSS REFERENCE TO RELATED APPLICATIONS

This application is a National Phase of International Application Number PCT/CN2014/082377, filed on Jul. 17, 2014, and claims priority of U.S. provisional application Ser. No. 61/856,005, filed on Jul. 18, 2013, entitled "Quinazoline derivatives, compositions thereof, and use as pharmaceuticals", each of which is incorporated herein by reference in its entirety.

FIELD OF THE INVENTION

This invention relates to novel quinazoline compounds and the pharmaceutically acceptable salts thereof. The compounds of the present invention may inhibit the epidermal growth factor receptor kinases thereby inhibiting the abnormal growth of certain cell types. The compounds of this invention are useful for the treatment of hyper-proliferative diseases such as cancer, in mammals and especially in humans. This invention also relates to the pharmaceutical compositions containing them and the use in the treatment of cancer.

BACKGROUND OF THE INVENTION

Protein tyrosine kinases are a class of enzymes that catalyze the transfer of a phosphate group from ATP to a hydroxyl group on a tyrosine residue located on a protein substrate. Since protein kinases play critical roles in various cellular activities, deregulation of protein kinase activity can lead to altered cellular properties, such as uncontrolled cell growth associated with cancer.

The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4(ErbB-4). Mutations affecting EGFR expression or activity could result in cancer.

Dysregulation of the epidermal growth factor receptor signal transduction pathway has been implicated in tumorigenesis and cancer progression thus making it a clinically relevant target for novel anticancer treatments. Several inhibitors of the epidermal growth factor receptor signaling pathway have demonstrated clinical efficacy in cancer treatment. Small molecules such as gefitinib, erlotinib and lapatinib, as well as anti-EGFR antibodies cetuximab, panitumumab and trastuzumab, have been approved for the treatment of EGFR-overexpressing lung cancers.

Because of the emerging disease-related roles of epidermal growth factor receptors, there is a continuing need for compounds which may be useful for treating and preventing a disease which responds to inhibition of epidermal growth factor receptor(s) and have at least one advantageous property selected from potency, stability, selectivity, toxicity, pharmacodynamics properties and pharmacokinetics properties as an alternative. In this regard, a novel class of epidermal growth factor receptor inhibitors is provided herein.

DISCLOSURE OF THE INVENTION

Disclosed herein are certain novel quinazoline derivatives, compositions thereof, and their use as pharmaceuticals.

In one aspect, disclosed herein is at least one compound of formula (I):

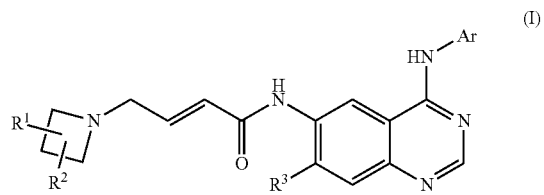

and/or at least one pharmaceutically acceptable salt thereof, wherein:

$R^1$ and $R^2$ are independently selected from hydrogen and $C_{1-6}$ alkyl, wherein alkyl is substituted with at least one substituent independently selected from the group consisting of hydroxyl, and $C_{1-6}$ alkoxy;

$R^3$ is selected from $C_{1-6}$ alkoxy, $C_{3-6}$ cycloalkoxy, tetrahydrofuran-3-yloxy, tetrahydrofuran-2-ylmethoxy, tetrahydrofuran-3-ylmethoxy, tetrahydropyran-4-yloxy, tetrahydropyran-4-ylmethoxy, (1,4-dioxan-2-yl)methoxy, and (3-oxabicyclo[3.1.0]hexan-6-yl)methoxy, wherein alkoxy and cycloalkoxy are independently unsubstituted or substituted with at least one substituent, such as one, two, three, or four substituents, independently selected from the group consisting of halogen, hydroxyl, $C_{1-6}$ alkyl, $C_{3-6}$ cycloalkyl and $C_{1-6}$ alkoxy;

Ar is selected from aryl, wherein aryl is substituted with at least one substituent, such as one, two, three, or four substituents, independently selected from the group consisting of halogen, hydroxyl and cyano.

The invention further relates to a pharmaceutical composition for the treatment of a hyperproliferative disorder in a mammal which comprises a therapeutically-effective amount of the compound of formula (I) and a pharmaceutically acceptable carrier.

The invention further relates to a method of treating a hyperproliferative disorder in a mammal which comprises administering to said mammal a therapeutically-effective amount of the compound of formula (I).

In a preferred embodiment, the method of treating hyperproliferative disorders includes those wherein said hyperproliferative disorder is cancer.

In another preferred embodiment, the method of treating hyperproliferative disorders includes those wherein said hyperproliferative disorder is noncancerous.

The invention further relates to a process for preparing a compound of the formula (I) or a pharmaceutically acceptable salt or prodrug thereof.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

DETAILED DESCRIPTION OF THE INVENTION

Figure 1:
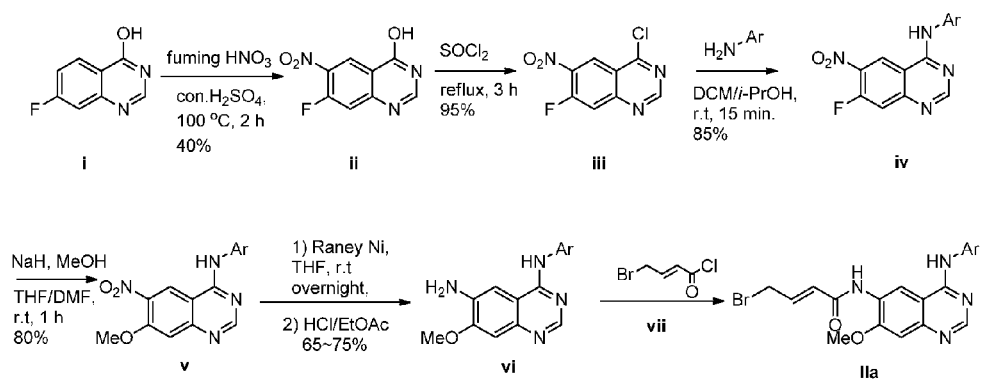
FIG. 1 shows a reaction scheme for the preparation of the compound of formula (I).
Figure 2:
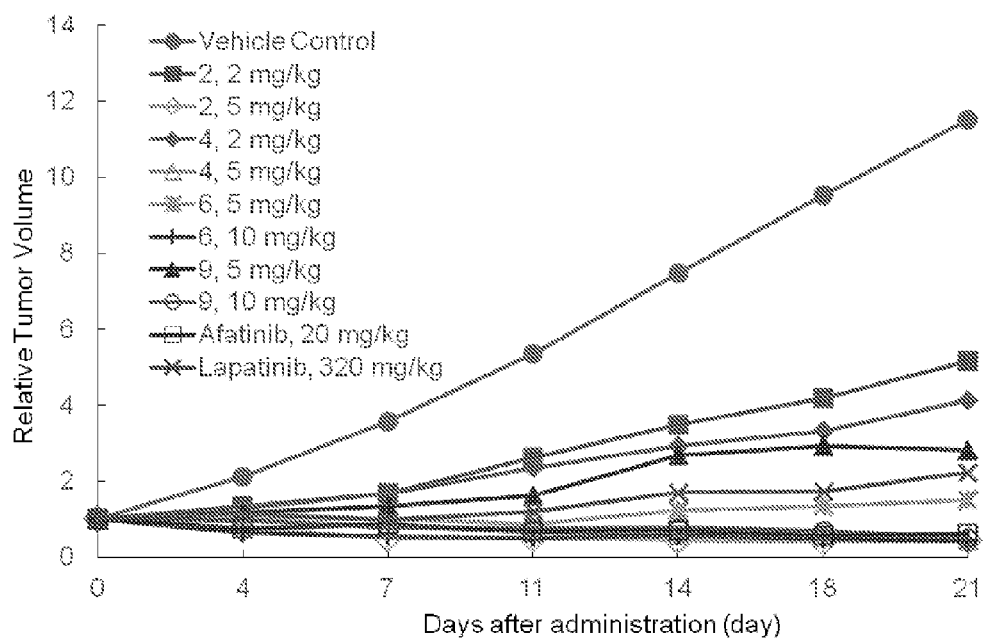
FIG. 2 shows the tumor inhibition of test compounds.

As used herein the following definitions are applicable.

The term "alkyl" refers to both branched and straight-chain saturated aliphatic hydrocarbon groups having the specified number of carbon atoms. Unless otherwise specified, "alkyl" refers to $C_{1-6}$alkyl. For example, $C_{1-6}$, as in "$C_{1-6}$ alkyl" is defined to include groups having 1, 2, 3, 4, 5, or 6 carbons in a linear or branched arrangement. For example, "$C_{1-6}$alkyl" includes but is not limited to methyl, ethyl, n-propyl, i-propyl, n-butyl, t-butyl, i-butyl, pentyl and hexyl.

The term "cycloalkyl" means a saturated aliphatic cyclic hydrocarbon group having the specified number of carbon atoms. Unless otherwise specified, "cycloalkyl" refers to $C_{3-6}$cycloalkyl. For example, "cycloalkyl" includes but is not limited to cyclopropyl, methyl-cyclopropyl, 2,2-dimethyl-cyclobutyl, 2-ethyl-cyclopentyl, and cyclohexyl.

The term "alkoxy" refers to either a cyclic or non-cyclic alkyl group of indicated number of carbon atoms attached through an oxygen bridge. "alkoxy" therefore encompasses the definitions of alkyl and cycloalkyl above. "Cycloalkoxy" refers to a cyclic alkyl group of indicated number of carbon atoms attached through an oxygen bridge.

The term "aryl" encompasses:

5- and 6-membered carbocyclic aromatic rings, for example, benzene;

bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" (or "halo") refers to fluorine, chlorine, bromine and iodine.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "administration of" and or "administering" at least one compound and/or at least one pharmaceutically acceptable salt should be understood to mean providing at least one compound and/or at least one pharmaceutically acceptable salt thereof to the individual in recognized need of treatment.

The term "effective amount" means the amount of the at least one compound and/or at least one pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

By "pharmaceutically acceptable" it is meant compatible with the other ingredients of the formulation and not unacceptably deleterious to the recipient thereof In one embodiment, disclosed herein is at least one compound of formula (I):

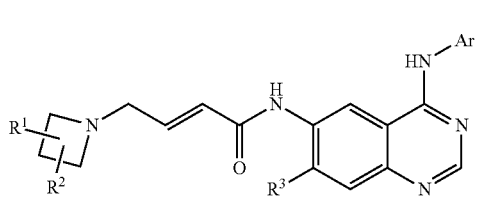

and/or at least one pharmaceutically acceptable salt thereof, wherein:

$R^1$ and $R^2$ are independently selected from hydrogen and $C_{1-6}$ alkyl, wherein alkyl is substituted with at least one substituent independently selected from the group consisting of hydroxyl, and $C_{1-6}$ alkoxy;

$R^3$ is selected from $C_{1-6}$ alkoxy, $C_{3-6}$ cycloalkoxy, tetrahydrofuran-3-yloxy, tetrahydrofuran-2-ylmethoxy, tetrahydrofuran-3-ylmethoxy, tetrahydropyran-4-yloxy, tetrahydropyran-4-ylmethoxy, (1,4-dioxan-2-yl)methoxy, and (3-oxabicyclo[3.1.0]hexan-6-yl)methoxy, wherein alkoxy and cycloalkoxy are independently unsubstituted or substituted with at least one substituent, such as one, two, three, or four substituents, independently selected from the group consisting of halogen, hydroxyl, $C_{1-6}$ alkyl, $C_{3-6}$ cycloalkyl and $C_{1-6}$ alkoxy;

Ar is selected from aryl, wherein aryl is substituted with at least one substituent, such as one, two, three, or four substituents, independently selected from the group consisting of halogen, hydroxyl and cyano.

In some embodiments, $R^2$ is hydrogen.

In some embodiments, $R^1$ is $C_{1-6}$ alkyl, wherein alkyl is substituted with at least one substituent independently selected from the group consisting of hydroxyl and $C_{1-6}$ alkoxy. In further some embodiments, $R^1$ is selected from hydroxymethyl, methoxymethyl and ethoxymethyl. In further some embodiments, $R^1$ is selected from hydroxymethyl and methoxymethyl.

In some embodiments, $R^3$ is selected from methoxy, ethoxy, methoxyethoxy, cyclopropylmethoxy, tetrahydrofuran-3-yloxy, tetrahydrofuran-2-ylmethoxy, tetrahydrofuran-3-ylmethoxy, tetrahydropyran-4-yloxy, tetrahydropyran-4-ylmethoxy, (1,4-dioxan-2-yl)methoxy, and (3-oxabicyclo[3.1.0]hexan-6-yl)methoxy.

In some embodiments, Ar is aryl, wherein aryl is substituted with at least one substituent, such as one, two, three, or four substituents, independently selected from the group consisting of fluorine, chlorine, bromine and iodine.

In some embodiments, Ar is 3-chloro-4-fluorophenyl.

Also provided is at least one compound, selected from:
(E)-N-(4-(3-chloro-4-fluorophenylamino)-7-methoxyquinazolin-6-yl)-4-(2-(hydroxymethyl) azetidin-1-yl)but-2-enamide;
(R,E)-N-(4-(3-chloro-4-fluorophenylamino)-7-methoxyquinazolin-6-yl)-4-(2-(methoxymethyl)azetidin-1-yl)but-2-enamide;
(S,E)-N-(4-(3-chloro-4-fluorophenylamino)-7-methoxyquinazolin-6-yl)-4-(2-(methoxymethyl)azetidin-1-yl)but-2-enamide;
(R,E)-N-(4-(3-chloro-4-fluorophenylamino)-7-ethoxyquinazolin-6-yl)-4-(2-(methoxymethyl)azetidin-1-yl)but-2-enamide;
(S,E)-N-(4-(3-chloro-4-fluorophenylamino)-7-ethoxyquinazolin-6-yl)-4-(2-(methoxymethyl)azetidin-1-yl)but-2-enamide.
(R,E)-N-(4-(3-chloro-4-fluorophenylamino)-7-(2-methoxyethoxy)quinazolin-6-yl)-4-(2-(methoxymethyl)azetidin-1-yl)but-2-enamide;
(S,E)-N-(4-(3-chloro-4-fluorophenylamino)-7-(2-methoxyethoxy)quinazolin-6-yl)-4-(2-(methoxymethyl)azetidin-1-yl)but-2-enamide;
(E)-N-(4-(3-chloro-4-fluorophenylamino)-7-(cyclopropylmethoxy)quinazolin-6-yl)-4-(2-(hydroxymethyl)azetidin-1-yl)but-2-enamide;
(R,E)-N-(4-(3-chloro-4-fluorophenylamino)-7-(cyclopropylmethoxy)quinazolin-6-yl)-4-(2-(methoxymethyl)azetidin-1-yl)but-2-enamide;
(S,E)-N-(4-(3-chloro-4-fluorophenylamino)-7-(cyclopropylmethoxy)quinazolin-6-yl)-4-(2-(methoxymethyl)azetidin-1-yl)but-2-enamide;
(E)-N-(4-(3-chloro-4-fluorophenylamino)-7-((S)-tetrahydrofuran-3-yloxy)quinazolin-6-yl)-4-(2-(hydroxymethyl)azetidin-1-yl)but-2-enamide;
(E)-N-(4-(3-chloro-4-fluorophenylamino)-7-((S)-tetrahydrofuran-3-yloxy)quinazolin-6-yl)-4-(2-(methoxymethyl)azetidin-1-yl)but-2-enamide;
(E)-N-(7-(((R)-1,4-dioxan-2-yl)methoxy)-4-(3-chloro-4-fluorophenylamino) quinazolin-6-yl)-4-(2-(hydroxymethyl)azetidin-1-yl)but-2-enamide;
(E)-N-(7-(((R)-1,4-dioxan-2-yl)methoxy)-4-(3-chloro-4-fluorophenylamino) quinazolin-6-yl)-4-((R)-2-(methoxymethyl)azetidin-1-yl)but-2-enamide;
(E)-N-(7-(((R)-1,4-dioxan-2-yl)methoxy)-4-(3-chloro-4-fluorophenylamino) quinazolin-6-yl)-4-((S)-2-(methoxymethyl)azetidin-1-yl)but-2-enamide;
(E)-N-(7-(((S)-1,4-dioxan-2-yl)methoxy)-4-(3-chloro-4-fluorophenylamino) quinazolin-6-yl)-4-(2-(hydroxymethyl)azetidin-1-yl)but-2-enamide;
(E)-N-(7-(((S)-1,4-dioxan-2-yl)methoxy)-4-(3-chloro-4-fluorophenylamino) quinazolin-6-yl)-4-(2-(methoxymethyl)azetidin-1-yl)but-2-enamide;
(E)-N-(7-((1R,5S,6R)-3-oxabicyclo[3.1.0]hexan-6-ylmethoxy)-4-(3-chloro-4-fluorophenylamino)quinazolin-6-yl)-4-(2-(hydroxymethyl)azetidin-1-yl)but-2-enamide;
(E)-N-(7-((1R,5S,6R)-3-oxabicyclo[3.1.0]hexan-6-ylmethoxy)-4-(3-chloro-4-fluorophenylamino)quinazolin-6-yl)-4-((R)-2-(methoxymethyl)azetidin-1-yl)but-2-enamide;
(E)-N-(7-((1R,5S,6R)-3-oxabicyclo[3.1.0]hexan-6-ylmethoxy)-4-(3-chloro-4-fluorophenylamino)quinazolin-6-yl)-4-((S)-2-(methoxymethyl)azetidin-1-yl)but-2-enamide;
and/or pharmaceutically acceptable salts thereof.

Some of the compounds of Formula (I) have asymmetric carbon atoms. Such diasteromeric mixtures can be separated into their individual diastereomers on the basis of their physical chemical differences by methods known per se., for example, by chromatography and/or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomers mixtures and pure enantiomers are considered as part of the invention.

The active compounds of this invention are potent inhibitors of the ErbB family of oncogenic and protooncogenic protein tyrosine kinases such as epidermal growth factor receptor (EGFR), ErbB2, HER3, or HER4 and thus are all adapted to therapeutic use as antiproliferative agents (e.g., anticancer) in mammals, particularly humans. In particular, the compounds of this invention are therapeutants or prophylactics for the treatment of a variety of human tumors (renal, liver, kidney, bladder, breast, gastric, ovarian, colorectal, prostate, pancreatic, lung, vulval, thyroid, hepatic carcinomas, sarcomas, glioblastomas, various head and neck tumors), and other hyperplastic conditions such as benign hyperplasia of the skin (e.g., psoriasis) or prostate (e.g., BPH). It is, in addition, expected that a quinazoline of the present invention may possess activity against a range of leukemias and lymphoid malignancies.

The active compounds may also be expected to be useful in the treatment of additional disorders in which aberrant expression ligand/receptor interactions, activation or signalling events related to various protein tyrosine kinases, whose activity is inhibited by the agents of Formula I, are involved.

Such disorders may include those of neuronal, glial, astrocytal, hypothalamic, and other glandular, macrophagal, epithelial, stromal, and blastocoelic nature in which aberrant function, expression, activation or signalling of the ErbB tyrosine kinases may be involved. In addition, compounds of Formula I may have therapeutic utility in inflammatory, angiogenic and immunologic disorders involving both identified and as yet unidentified tyrosine kinases which are inhibited by compounds of Formula (I).

In accordance with the foregoing, the present disclosure also provides:

(1) a compound disclosed herein for use as a pharmaceutical;

(2) a compound disclosed herein for use as an ErbB family of receptor kinase inhibitor, for example, for use in any of the particular indications set forth above;

(3) a pharmaceutical composition, e.g. for use in any of the indications herein set forth above, comprising at least one compound disclosed herein as active ingredient together with one or more pharmaceutically acceptable diluents or carriers;

(4) a method for treatment of any particular indication set forth above in a subject in need thereof which comprises administering an effective amount of at least one compound disclosed herein or at least one pharmaceutical composition comprising thereof;

(5) the use of a compound disclosed herein for making a medicament for treatment or prevention of a disease or condition in which ErbB family of receptor kinase play a role or is implicated;

(6) the method as defined above under (4) comprising co-administration, e.g. concomitantly or in sequence, of a therapeutically effective amount of a compound disclosed herein and one or more additional drug substances, said additional drug substance being useful in any of the particular indications set forth above;

(7) a composition comprising a therapeutically effective amount of at least one compound disclosed herein and at least one additional drug substance, wherein said additional drug substance is useful in any of the particular indications set forth above;

(8) use of a compound disclosed herein for making a medicament for treatment or prevention of a disease which responds to inhibition of the ErbB family of receptor kinase;

(9) the use according to (8), wherein the disease to be treated is selected from head and neck cancer, lung cancer (e.g., NSCLC), breast cancer, colon cancer, ovarian cancer, bladder cancer, gastric cancer, kidney cancer, skin cancer, pancreatic cancer, leukemias, lymphomas, esophageal cancer, uterine cancer or prostate cancer.

(10) the use according to (8) or (9), wherein the compound is a pharmaceutically acceptable salt of any one of the examples disclosed herein;

(11) a method for the treatment of a disease which responds to inhibition of the ErbB family of receptor kinase, such as a disease selected from head and neck cancer, lung cancer (e.g., NSCLC), breast cancer, colon cancer, ovarian cancer, bladder cancer, gastric cancer, kidney cancer, skin cancer, pancreatic cancer, leukemias, lymphomas, esophageal cancer, uterine cancer or prostate cancer, comprising administering an effective amount of at least one compound disclosed herein and/or a pharmaceutically acceptable salt thereof. In some examples, the compounds of the disclosure may be used alone or in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls A G, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the disclosure may be administered as the sole active ingredient, or together with other drugs useful against neoplastic diseases or useful in immunomodulating regimens. For example, the compounds of the disclosure may be used in accordance with the disclosure in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

EXAMPLES

Various methods may be developed for synthesizing the at least one compound of formula (I) and/or at least one pharmaceutically acceptable salt thereof. Representative methods for synthesizing the at least one compound of formula (I) and/or at least one pharmaceutically acceptable salt thereof are provided in the Examples. It is noted, however, that the at least one compound of formula (I) and/or at least one pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of the at least one compound of formula (I) and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

The at least one compound of formula (I) and/or at least one pharmaceutically acceptable salt thereof may be conveniently prepared, or as solvates (e.g. hydrates). Hydrates of the at least one compound of formula I and/or at least one pharmaceutically acceptable salt thereof may be conveniently prepared by recrystallization from an aqueous/organic solvent mixture, using organic solvents such as dioxin, tetrahydrofuran and/or methanol.

The compounds of formula (I) can also be prepared as their individual stereoisomers by reacting a racemic mixture of the compounds with an optically active resolving agent to form a pair of diastereoisomeric compounds, separating the diastereomers, and recovering the optically pure enantiomer. While resolution of enantiomers can be carried out using covalent diasteromeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, for example, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, ninhydrin, or p-anisaldehyde solution. Flash column chromatography was performed on silica gel (230-400 mesh, Merck).

Synthetic Schemes

The at least one compound of formula (I) and/or at least one pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions disclosed below, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example, see T. W. Greene and P. G. M. Wuts in "Protective Groups in Organic Chemistry" John Wiley and Sons, 1991.

Synthetic methods for preparing the compounds in the present disclosure are illustrated in the following Schemes and Examples. Starting materials are commercially available or may be made according to procedures known in the art or as illustrated herein.

Preparation of Compound of Formula (I)

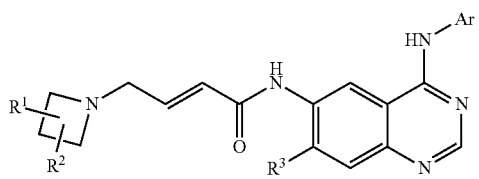
(I)

Compound of formula (I) could be assembled by combination of 4-bromo-enamide (II) with properly substituted amine (III) via nucleophilic substitution reaction in a polar solvent such as DMF in the presence of base such as K$_2$CO$_3$.

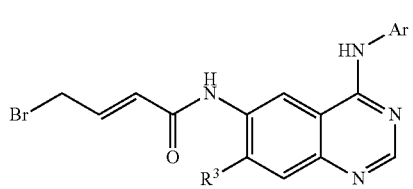
II

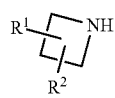
III

Synthesis of Intermediate IIa

Intermediate IIa may be prepared as illustrated in the following FIG. 1. 4-Chloro-7-fluoro-6-nitroquinazoline (iii) can be prepared by methods similar to those described in J. Med. Chem. 1996, 39, 918-928. Nitration of fluoroquinazoline (i) provides 7-fluoro-6-nitro-3H-quinazolin-4-one (ii), which can be treated with thionyl chloride to give 4-chloroquinazoline (iii). Combination of 4-chloro-quinazoline (iii) with properly substituted aniline in a solvent such as isopropanol leads to 4-anilino-quinazoline (iv). Treatment of 7-fluoro-quinazoline (iv) with sodium methoxide provides 7-methoxy-quinazoline (v). Hydrogenation of the 6-nitro compound (v) in the presence of a catalyst such as Raney Nickel provides the 6-amino analog (vi). The 6-aminoquinazoline (vi) may be reacted with a haloEGFRenoyl chloride, such as 4-bromo-but-2-enoyl chloride (vii), to provide 4-bromo-eneamide IIa. HaloEGFRenoyl chloride are readily accessible through known procedures, such as treatment of alkenoic acid with halogenating agent such as NBS yielding the corresponding haloEGFRenoic acid, which may in turn be treated with oxalyl chloride to provide the desired haloEGFRenoyl chloride.

Intermediates shown in the following Scheme 1 can be synthesized by using the same procedure as described for intermediate IIa by replacing methanol with the appropriate alcohols which are either commercially available or readily accessible through known procedures.

Scheme 1

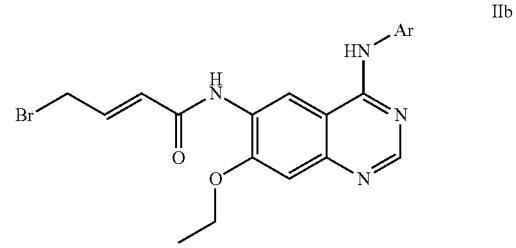
IIb

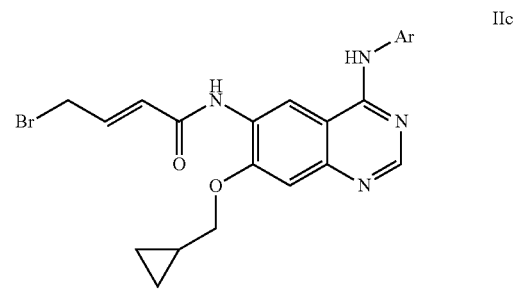
IIc

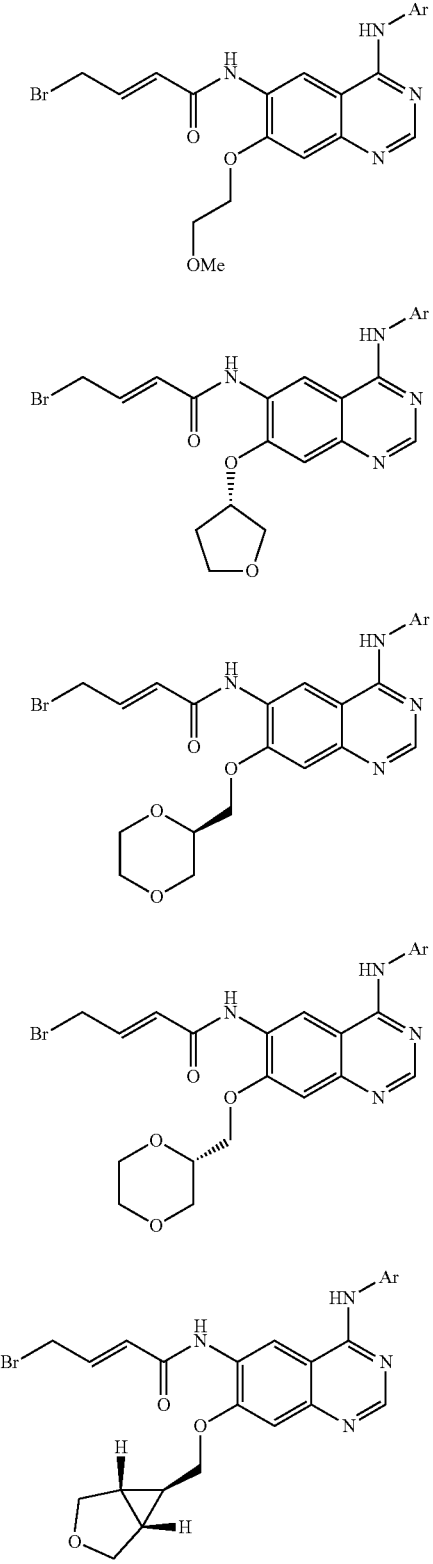

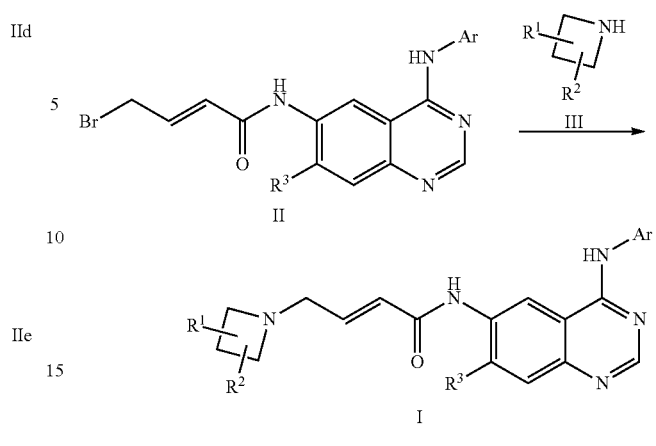

In some cases the order of carrying out the foregoing reaction schemes may be varied to facilitate the reaction or to avoid unwanted reaction products. The following examples are provided so that the invention might be more fully understood. These examples are illustrative only and shall not be construed as limiting the invention in any way.

Preparation of Intermediates

Intermediate A

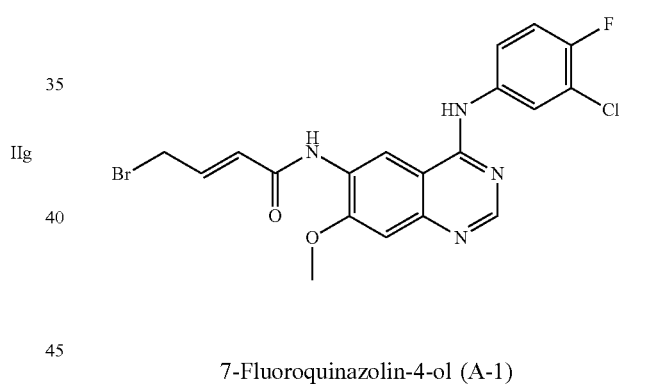

7-Fluoroquinazolin-4-ol (A-1)

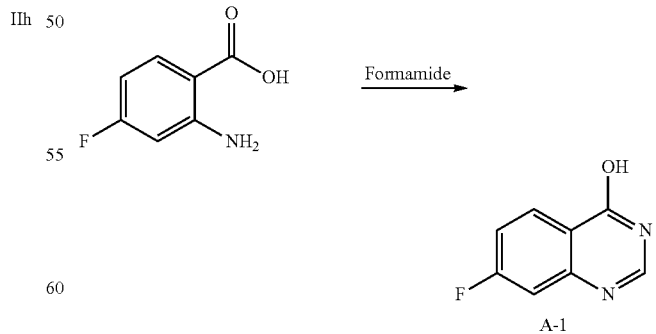

Finally, treatment of Intermediate II with a secondary amine III, which are commercially available or readily accessible through known procedures, provides compound I.

A mixture of 2-amino-4-fluorobenzoic acid (3.00 g, 19.3 mmol) in formamide (30 mL) was heated at 150° C. for 6 hours. The mixture was poured into ice-water (1/1) (250 mL). The solid was collected by filtration, washed with water and dried to give the title compound (A-1) as white solid. MS-ESI (m/z): 165 [M+H]⁺.

7-Fluoro-6-nitroquinazolin-4-ol (A-2)

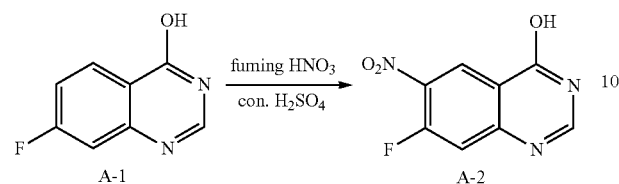

A solution of 7-fluoroquinazolin-4-ol (A-1) in concentrated $H_2SO_4$ (100 mL) and fuming $HNO_3$ (100 mL) was heated at 100° C. for 1 h. After cooling, the solution was poured into ice-water (1.5 L) to give a mixture of 6- and 8-nitroquinazolin-4-ol. Recrystallization of the mixture from AcOH gave title compound (A-2) as yellow solid. MS-ESI (m/z): 210 [M+H].

4-Chloro-7-fluoro-6-nitroquinazoline (A-3)

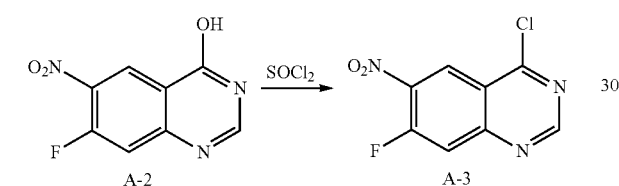

A suspension of 7-fluoro-6-nitroquinazolin-4-ol (A-2) (10.45 g, 50.00 mmol) in $SOCl_2$ (200 mL) containing catalytic amount of DMF was heated under reflux for 3 h to give a clear solution. The $SOCl_2$ was removed under vacuum to give the crude title compound (A-3) which was directly used in next step.

N-(3-chloro-4-fluorophenyl)-7-fluoro-6-nitroquinazolin-4-amine (A-4)

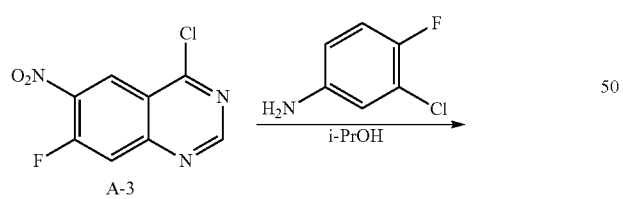

To a solution of crude 4-chloro-7-fluoro-6-nitroquinazoline (A-3) in DCM (100 mL) was added a solution of 3-chloro-4-fluorobenzenamine (7.97 g, 54.8 mmol) in i-PrOH (250 mL). The resulting mixture was stirred at r.t. for 15 min. Petroleum ether (800 mL) was added to ensure complete precipitation. Solid was collected by filtration to give the title compound (A-4). MS-ESI (m/z): 337 [M+H]⁺.

N-(3-chloro-4-fluorophenyl)-7-methoxy-6-nitroquinazolin-4-amine (A-5)

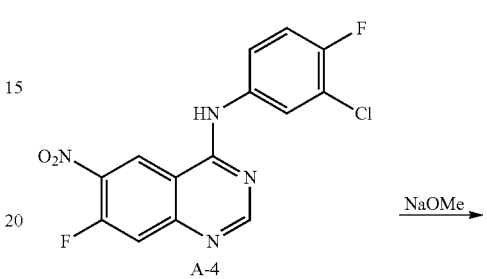

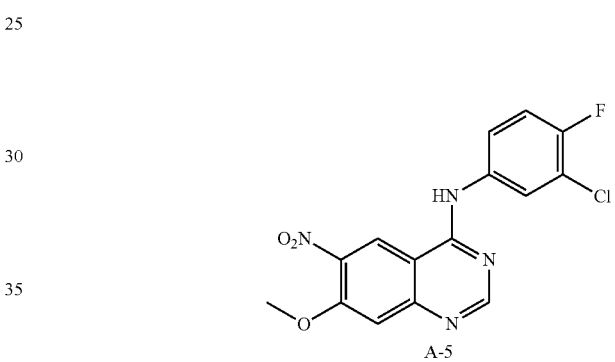

To a solution of NaOMe (28.0 g, 518 mmol) in of dry MeOH (1.5 L) under $N_2$ on a cooling bath was added N-(3-chloro-4-fluorophenyl)-7-fluoro-6-nitroquinazolin-4-amine (A-4) (72.76 g, 219 mmol). The cooling bath was removed and the mixture was heated at reflux for 1 h. The reaction was cooled to r.t. and quenched with water until the product precipitated. The solid was collected by filtration and washed with water and $Et_2O$, and dried to give the title compound (A-5) as yellow solid. MS-ESI (m/z): 349 [M+H]⁺.

N⁴-(3-chloro-4-fluorophenyl)-7-methoxyquinazoline-4,6-diamine (A-6)

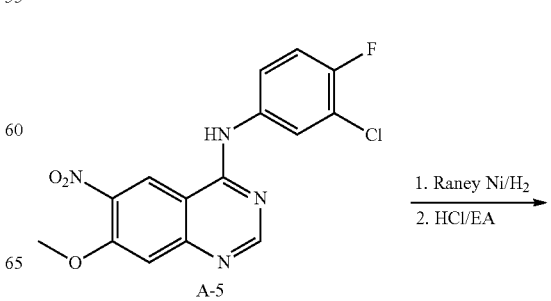

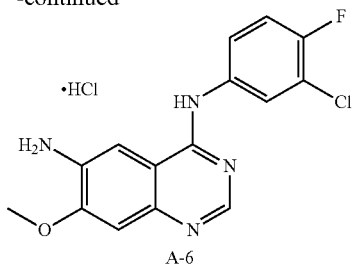

To a solution of N-(3-chloro-4-fluorophenyl)-7-methoxy-6-nitroquinazolin-4-amine (A-5) (31.81 g, 91.22 mmol) in THF was added Raney Ni (4 g). The mixture was stirred at r.t. for 12 h under H$_2$ balloon. The catalyst was removed by filtration. The filtrates were concentrated to about 50 mL. Then HCl/EA was added slowly followed by MTBE. The precipitate was collected by filtration, dried to give the title compound (A-6) as hydrochloride. MS-ESI (m/z): 319 [M+H]$^+$.

(E)-4-bromo-N-(4-(3-chloro-4-fluorophenylamino)-7-methoxyquinazolin-6-yl)but-2-enamide (Intermediate A)

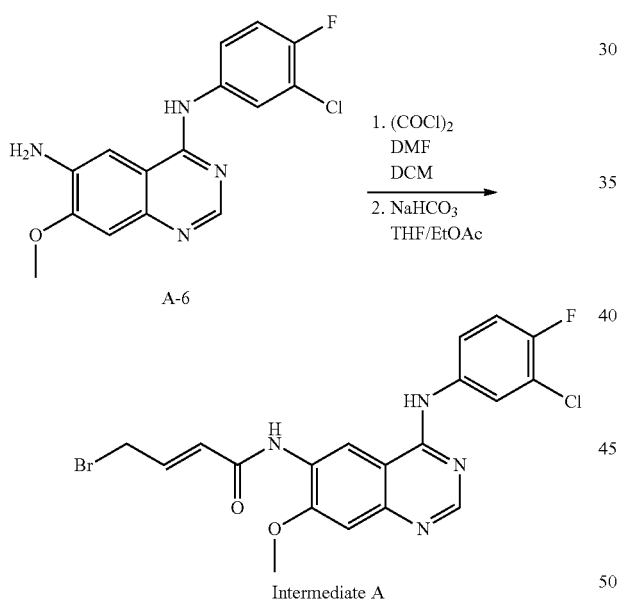

To a solution of crotonic acid (10.0 g, 116 mmol) in CCl$_4$ (100 mL) was added N-bromosuccinimide (21.4 g, 120 mmol) followed by benzoyl peroxide (0.20 g, 0.83 mmol). The mixture was refluxed for 4.5 h, and then cooled to r.t. The mixture was stored in fridge overnight. The crystals were filtered off and the filtrate was evaporated. The residue was recrystallized from hexane to give (E)-4-bromobut-2-enoic acid as white solid.

To a solution of (E)-4-bromobut-2-enoic acid (0.825 g, 5.00 mmol) in DCM (10 mL) was added (COCl)$_2$ (1.27 g, 10.0 mmol) followed by DMF (about 50 μL). The mixture was stirred at r.t. for 4.5 h. Solvents were evaporated, the residue was re-dissolved in 5 mL of THF (solution A).

To a stirred mixture of A-6 (800 mg, 2.25 mmol) in a mixture of THF (10 mL), EtOAc (10 mL) and saturated NaHCO$_3$ (40 mL) was added solution A dropwise at 0° C. Then the mixture was stirred at r.t. for 30 min. The organic layer was separated and the aqueous layer was extracted with EtOAc (40 mL). The combined organic layer was washed with brine, dried over Na$_2$SO$_4$ and evaporated. The residue was purified by column chromatography (hexanes:EtOAc=2:1) to give the title compound as yellow solid. MS-ESI (m/z): 465 [M+1]$^+$.

Intermediate B (E)-4-bromo-N-(4-((3-chloro-4-fluorophenyl)amino)-7-ethoxyquinazolin-6-yl)but-2-enamide (Intermediate B)

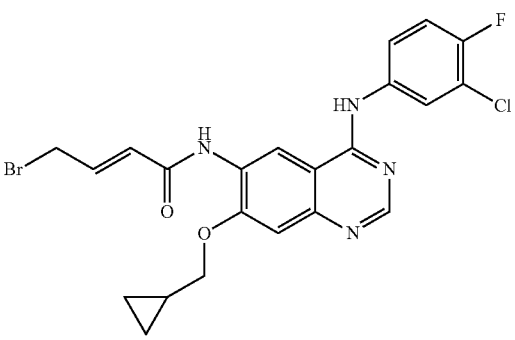 [SMILES: O=C(/C=C/CBr)Nc1cc2c(Nc3ccc(F)c(Cl)c3)ncnc2cc1OCC1CC1]

Intermediate B was prepared by using the same procedure as described for Intermediate A by replacing methanol with ethanol.

Intermediate C (E)-4-bromo-N-(4-((3-chloro-4-fluorophenyl)amino)-7-(cyclopropylmethoxy) quinazolin-6-yl)but-2-enamide (Intermediate C)

Intermediate C was prepared by using the same procedure as described for Intermediate A by replacing methanol with cyclopropylmethanol.

Intermediate D

(E)-4-bromo-N-(4-((3-chloro-4-fluorophenyl)amino)-7-(2-methoxyethoxy) quinazolin-6-yl)but-2-enamide (Intermediate D)

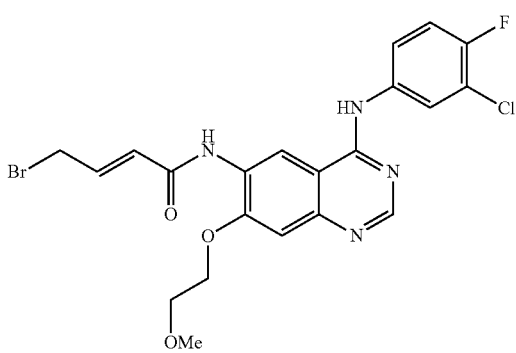 [SMILES: COCCOc1cc2ncnc(Nc3ccc(F)c(Cl)c3)c2cc1NC(=O)/C=C/CBr]

Intermediate D was prepared by using the same procedure as described for Intermediate A by replacing methanol with 2-methoxyethanol.

Intermediate E

(S,E)-4-bromo-N-(4-((3-chloro-4-fluorophenyl)amino)-7-((tetrahydrofuran-3-yl)oxy)quinazolin-6-yl)but-2-enamide (Intermediate E)

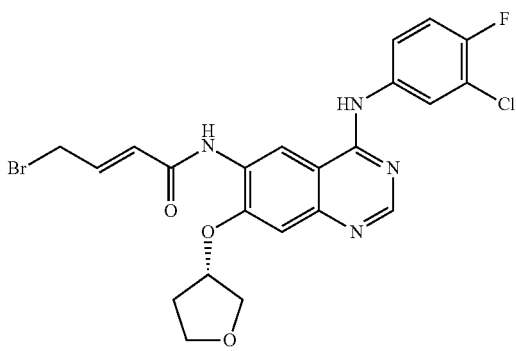 [SMILES: O=C(/C=C/CBr)Nc1cc2c(Nc3ccc(F)c(Cl)c3)ncnc2cc1O[C@H]1CCOC1]

Intermediate E was prepared by using the same procedure as described for Intermediate A by replacing methanol with (S)-tetrahydrofuran-3-ol.

Intermediate F

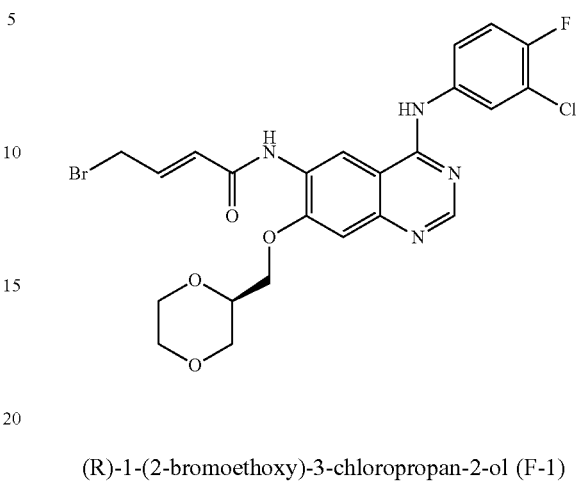

(R)-1-(2-bromoethoxy)-3-chloropropan-2-ol (F-1)

To a solution of 2-bromoethanol (12.86 mL, 191.8 mmol) and $BF_3 \cdot Et_2O$ (0.45 mL, 3.2 mmol) was added (R)-2-(chloromethyl)oxirane dropwise at 45° C. The reaction mixture was heated at 45° C. for 2 h. After cooled to r.t., diethyl ether (100 mL) was added to the mixture. The solution was washed with water, dried over $Na_2SO_4$ and concentrated to give the title compound (F-1) as light brown liquid.

(R)-2-((2-bromoethoxy)methyl)oxirane (F-2)

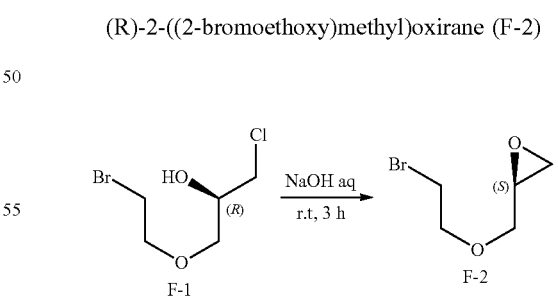

(R)-1-(2-bromoethoxy)-3-chloropropan-2-ol (F-1) (11 g, 64 mmol) was added dropwise to a stirred solution of NaOH (6.36 g, 159 mmol) in water (7.6 mL) at 0° C. The mixture was stirred at 25° C. for 2 h. Then diethyl ether and water were added. The organic layer was separated and washed with water, dried over sodium sulfate and concentrated to give the title compound (F-2) as light brown liquid.

(S)-(1,4-dioxan-2-yl)methanol (F-3)

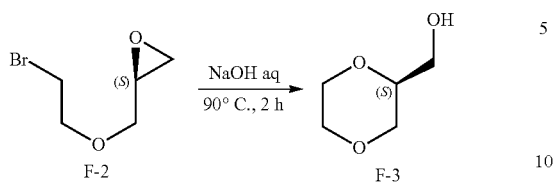

(R)-2-((2-bromoethoxy)methyl)oxirane (F-2) (5.5 g, 41 mmol) was added to an aqueous solution of NaOH (4.09 g, 102 mmol, 40 mL) at r.t. The mixture was heated to 90° C. and stirred for 2 h. The resulting mixture was saturated by adding solid $K_2CO_3$, and extracted with DCM (6×40 mL). The combined organic layer was dried over $Na_2SO_4$ and concentrated. The residue was purified by column chromatography with EtOAc/petroleum ether (2:1-3:1) to give the title compound (F-3) as clear liquid.

(R,E)-N-(7-((1,4-dioxan-2-yl)methoxy)-4-(3-chloro-4-fluorophenylamino) quinazolin-6-yl)-4-bromobut-2-enamide (Intermediate F)

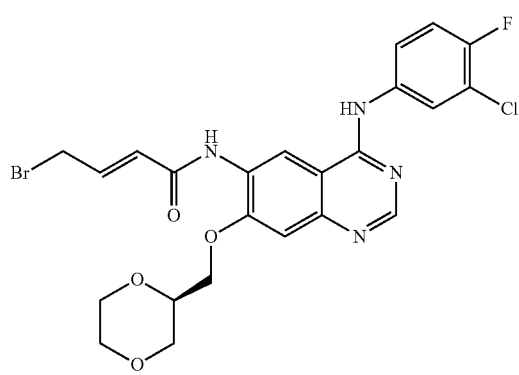 [SMILES: O=C(/C=C/CBr)Nc1cc2c(Nc3ccc(F)c(Cl)c3)ncnc2cc1OC[C@H]1COCCO1]

Intermediate F was prepared by using the same procedure as Intermediate A by replacing methanol with F-3. MS-ESI (m/z): 551 (M+1)$^+$.

Intermediate G (S,E)-N-(7-((1,4-dioxan-2-yl)methoxy)-4-((3-chloro-4-fluorophenyl)amino) quinazolin-6-yl)-4-bromobut-2-enamide (Intermediate G)

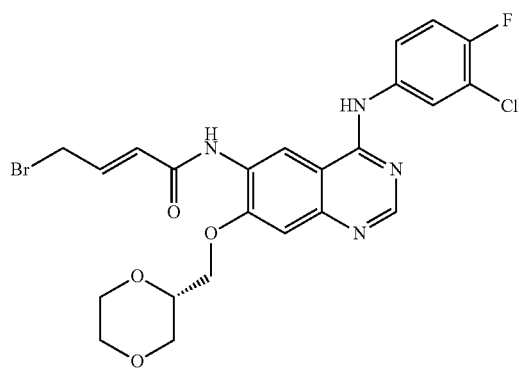 [SMILES: O=C(/C=C/CBr)Nc1cc2c(Nc3ccc(F)c(Cl)c3)ncnc2cc1OC[C@@H]1COCCO1]

Intermediate G was prepared by using the same procedure as described for Intermediate F by replacing (R)-2-(chloromethyl)oxirane with (S)-2-(chloromethyl)oxirane.

Intermediate H

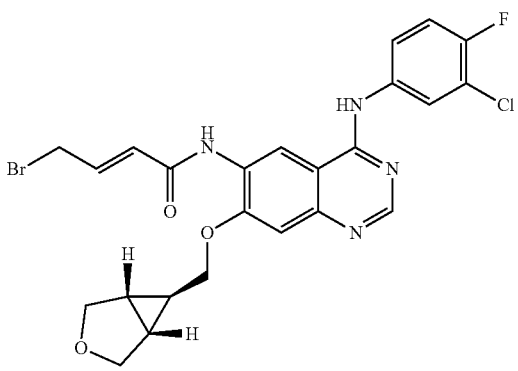 [SMILES: O=C(/C=C/CBr)Nc1cc2c(Nc3ccc(F)c(Cl)c3)ncnc2cc1OC[C@H]1[C@@H]2COC[C@@H]21]

(1R,5S,6R)-ethyl 3-oxabicyclo[3.1.0]hexane-6-carboxylate (H-1)

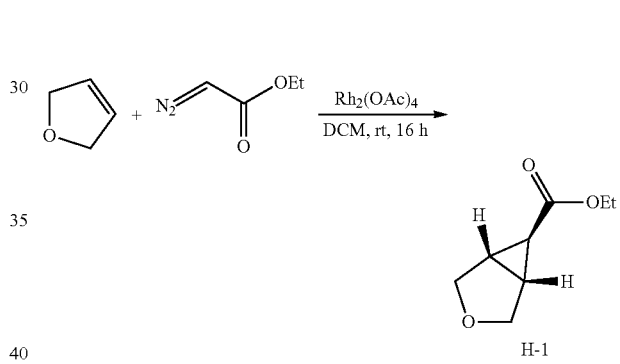

To a solution of 2,5-dihydro-furan (7.00 g, 100 mmol) in DCM (100 mL) was added $Rh_2(OAc)_4$ (0.22 g, 0.50 mmol) in one portion To the above solution was added a solution of ethyl 2-diazoacetate (12.0 mL, 0.1 mol) in DCM (50 mL) dropwise over 2.5 h. The reaction mixture was stirred at r.t. for 15 h. Then silica gel (20 g) was added to the mixture, after stirring vigorously for 5 min, the mixture was concentrated in vacuo and purified by flash column chromatography, eluted with hexanes/EtOAc (10:0-10:1) to give the title compound H-1 (6.0 g).

(1R,5S,6s)-3-oxabicyclo[3.1.0]hexan-6-ylmethanol (H-2)

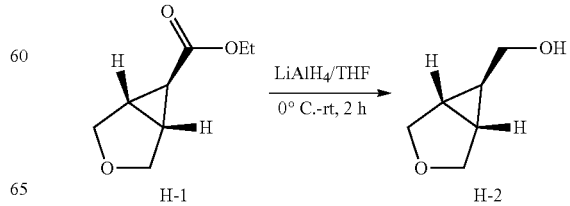

To a solution of H-1 (3.10 g, 20.0 mmol) in THF (40 mL) at 0° C. was added a solution of LiAlH$_4$ in THF (15.0 mL, 2.0 M, 30.0 mmol) dropwise. The mixture was warmed to r.t. and stirred for 1 h. After re-cooling to 0° C., NaSO$_4$.10H$_2$O (10 g) was added to the above mixture in 3 portions with precaution, the mixture was vigorously stirred for 1 h, and dried over MgSO$_4$. Filtration and concentration in vacuo gave the title compound H-2 (2.1 g).

(E)-N-(7-(((1R,5S,6r)-3-oxabicyclo[3.1.0]hexan-6-ylmethoxy)-4-(3-chloro-4-fluorophenylamino) quinazolin-6-yl)-4-bromobut-2-enamide (Intermediate H)

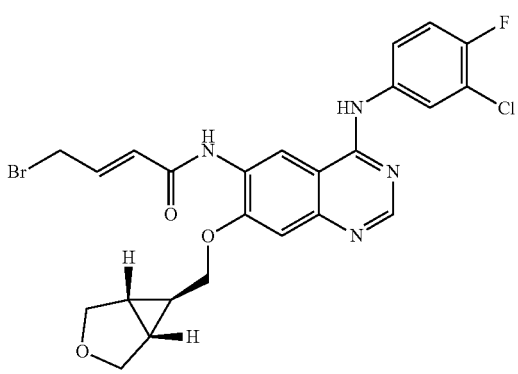 [SMILES: O=C(/C=C/CBr)Nc1cc2c(Nc3ccc(F)c(Cl)c3)ncnc2cc1OC[C@H]1[C@@H]2COC[C@@H]21]

Intermediate H was prepared by using the same procedure as Intermediate A by replacing methanol with H-2.

Example 1

(E)-N-(4-(3-chloro-4-fluorophenylamino)-7-methoxyquinazolin-6-yl)-4-(2-(hydroxymethyl) azetidin-1-yl)but-2-enamide (1)

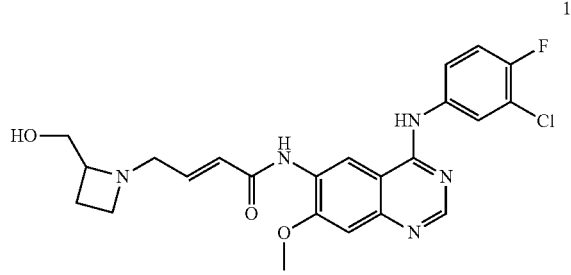 [SMILES: COc1cc2ncnc(Nc3ccc(F)c(Cl)c3)c2cc1NC(=O)/C=C/CN1CCC1CO]

Azetidin-2-ylmethanol hydrochloride (1a)

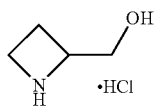

The title compound was prepared by using the same procedure as described in *J. Med. Chem.* 2008, 51, 948-956.

(E)-N-(4-(3-chloro-4-fluorophenylamino)-7-methoxyquinazolin-6-yl)-4-(2-(hydroxymethyl) azetidin-1-yl)but-2-enamide (1)

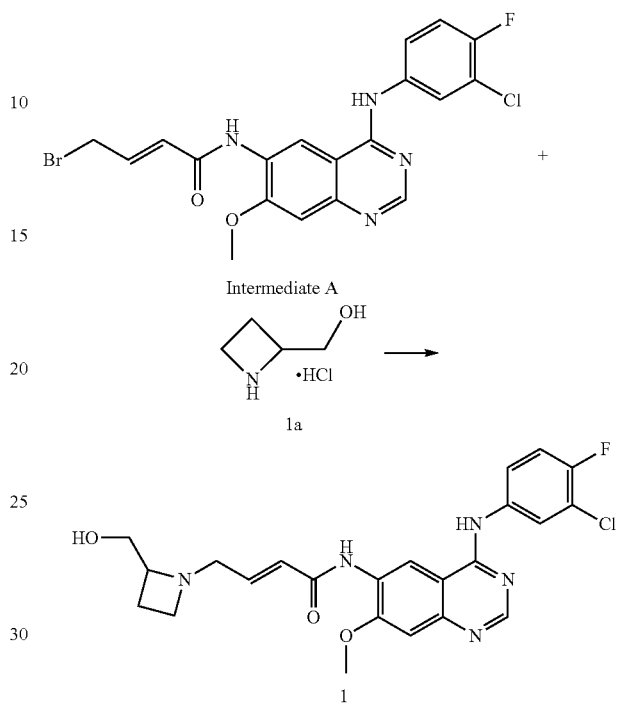

A mixture of azetidin-3-ylmethanol hydrochloride (1a) (50 mg, 0.4 mmol), Na$_2$CO$_3$ (100 mg, 0.8 mmol) in 3 mL DMF was stirred at r.t. for 0.5 h, and intermediate A (80 mg, 0.2 mmol) was added. The mixture was stirred at r.t for 1 h. The reaction was quenched with water (30 mL), and extracted with EtOAc (2×50 mL). The extracts were washed with water, brine, dried and concentrated. The residue was purified by column chromatography eluting with DCM/MeOH (15:1) to give the title compound (1) 40 mg as a yellow solid. MS-ESI (m/z): 472 [M+1]$^+$.

Example 2

(R,E)-N-(4-(3-chloro-4-fluorophenylamino)-7-methoxyquinazolin-6-yl)-4-(2-(methoxymethyl)azetidin-1-yl)but-2-enamide (2)

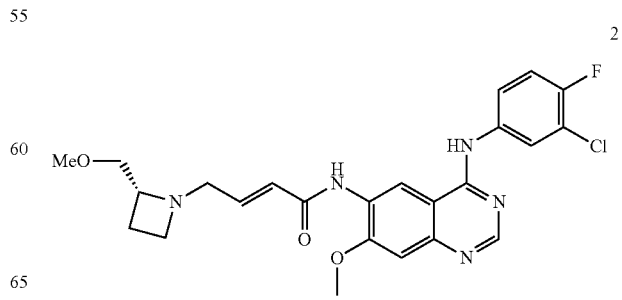

(R)-tert-butyl 2-(hydroxymethyl)azetidine-1-carboxylate (2a)

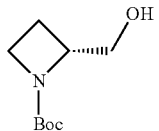

2a

The title compound was prepared starting from commercial available dibenzyl ester of D-aspartic acid using the same procedure as described in *Tetrahedron: Asymmetry* 1998, 9, 2791-2794.

(R)-tert-butyl 2-(methoxymethyl)azetidine-1-carboxylate (2b)

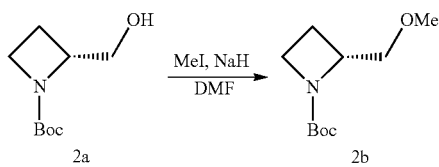

A solution of (R)-tert-butyl 2-(hydroxymethyl)azetidine-1-carboxylate (2a) (510 mg, 2.73 mmol) in 10 mL DMF was added NaH (60% 218 mg, 5.46 mmol) in portions at 0° C., and stirred for 0.5 hour. MeI (581 mg, 4.09 mmol) was added to the mixture and warmed to r.t. in 2 h. The reaction was quenched with ice-water (50 mL) and extracted with EtOAc (35 mL×3). The extracts were washed with brine (35 mL×2), dried over $Na_2SO_4$ and concentrated. The residue was purified by column chromatography, eluted with hexanes/EtOAc (6:1) to give 2b (260 mg) as colourless oil. MS-ESI (m/z): 202 $[M+1]^+$.

(R)-2-(methoxymethyl)azetidine trifluoroacetic acid salt (2c)

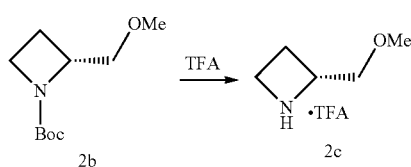 [SMILES: COC[C@H]1CCN1C(=O)OC(C)(C)C ; COC[C@H]1CCN1]

To a solution of tert-butyl 2-(methoxymethyl)azetidine-1-carboxylate (260 mg, 1.29 mmol) in DCM (5 mL) was added trifluoroacetic acid (1.5 mL). The mixture was stirred at r.t. for 1 h. The reaction mixture was concentrated to give crude product of 2c and used in next step without purification. MS-ESI (m/z): 102 $[M+1]^+$.

(R,E)-N-(4-(3-chloro-4-fluorophenylamino)-7-methoxyquinazolin-6-yl)-4-(2-(methoxymethyl)azetidin-1-yl)but-2-enamide (2)

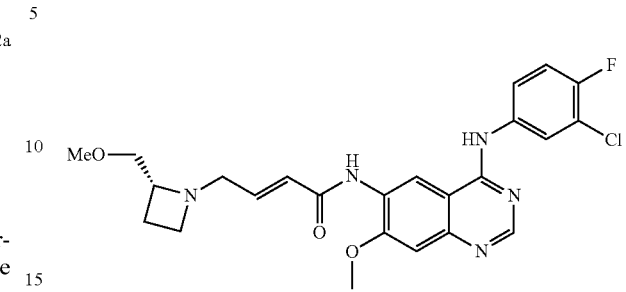

The title compound was prepared by using the same procedure as described for Example 1 by replacing 1a with 2c. MS-ESI (m/z): 486 $[M+1]^+$.

Example 3

(S,E)-N-(4-(3-chloro-4-fluorophenylamino)-7-methoxyquinazolin-6-yl)-4-(2-(methoxymethyl)azetidin-1-yl)but-2-enamide (3)

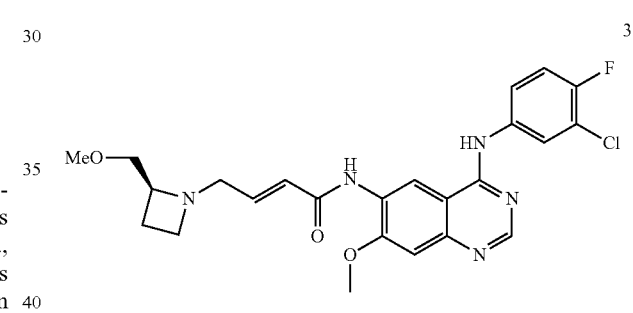

The title compound was prepared by using the same procedure as described for Example 2 by replacing dibenzyl ester of D-aspartic acid with dibenzyl ester of L-aspartic acid. MS-ESI (m/z): 486 $[M+1]^+$.

Example 4

(R,E)-N-(4-(3-chloro-4-fluorophenylamino)-7-ethoxyquinazolin-6-yl)-4-(2-(methoxymethyl)azetidin-1-yl)but-2-enamide (4)

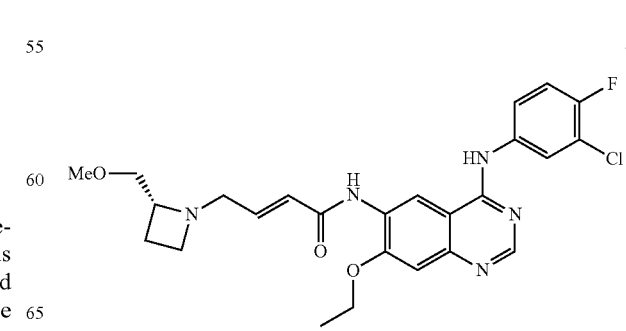

The title compound was prepared by using the same procedure as described for Example 2 by replacing intermediate A with intermediate B. MS-ESI (m/z): 500 [M+H]$^+$.

Example 5

(S,E)-N-(4-(3-chloro-4-fluorophenylamino)-7-ethoxyquinazolin-6-yl)-4-(2-(methoxymethyl)azetidin-1-yl)but-2-enamide (5)

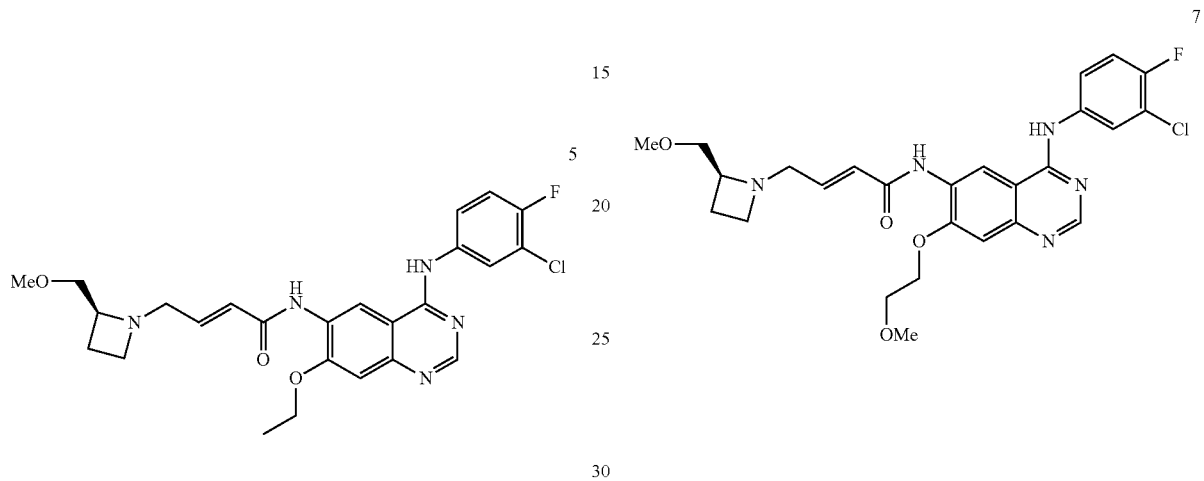

The title compound was prepared by using the same procedure as described for Example 3 by replacing intermediate A with intermediate B. MS-ESI (m/z): 500 [M+H]$^+$.

Example 6

(R,E)-N-(4-(3-chloro-4-fluorophenylamino)-7-(2-methoxyethoxy)quinazolin-6-yl)-4-(2-(methoxymethyl)azetidin-1-yl)but-2-enamide (6)

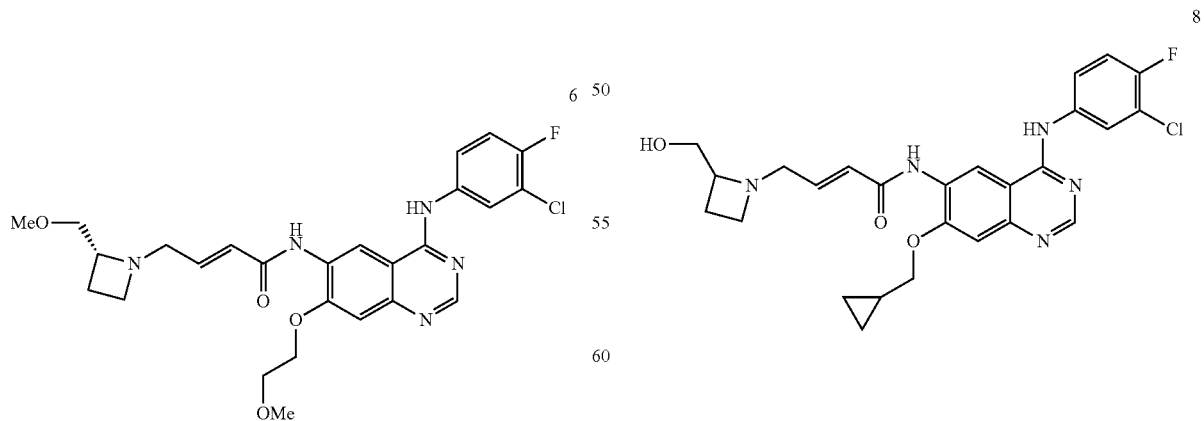

The title compound was prepared by using the same procedure as described for Example 2 by replacing intermediate A with intermediate D. MS-ESI (m/z): 530 [M+H]$^+$.

Example 7

(S,E)-N-(4-(3-chloro-4-fluorophenylamino)-7-(2-methoxyethoxy)quinazolin-6-yl)-4-(2-(methoxymethyl)azetidin-1-yl)but-2-enamide (7)

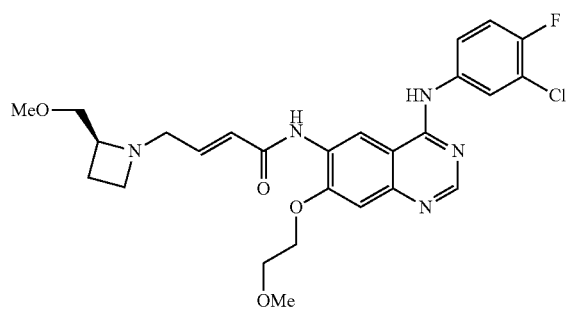

The title compound was prepared by using the same procedure as described for Example 3 by replacing intermediate A with intermediate D. MS-ESI (m/z): 530 [M+H]$^+$.

Example 8

(E)-N-(4-(3-chloro-4-fluorophenylamino)-7-(cyclopropylmethoxy)quinazolin-6-yl)-4-(2-(hydroxymethyl)azetidin-1-yl)but-2-enamide (8)

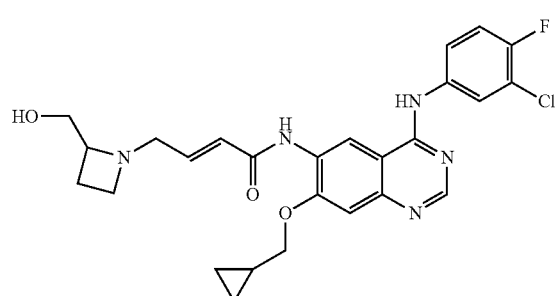

The title compound was prepared by using the same procedure as described for Example 1 by replacing intermediate A with intermediate C. MS-ESI (m/z): 512 [M+H]$^+$.

Example 9

(R,E)-N-(4-(3-chloro-4-fluorophenylamino)-7-(cyclopropylmethoxy)quinazolin-6-yl)-4-(2-(methoxymethyl)azetidin-1-yl)but-2-enamide (9)

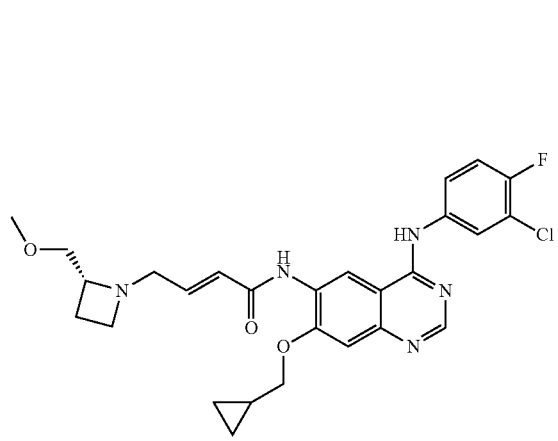

The title compound was prepared by using the same procedure as described for Example 2 by replacing intermediate A with intermediate C. MS-ESI (m/z): 526 [M+H]⁺.

Example 10

(S,E)-N-(4-(3-chloro-4-fluorophenylamino)-7-(cyclopropylmethoxy)quinazolin-6-yl)-4-(2-(methoxymethyl)azetidin-1-yl)but-2-enamide (10)

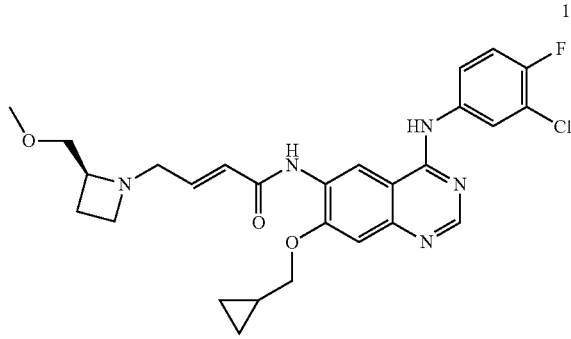

The title compound was prepared by using the same procedure as described for Example 3 by replacing intermediate A with intermediate C. MS-ESI (m/z): 526 [M+H]⁺.

Example 11

(E)-N-(4-(3-chloro-4-fluorophenylamino)-7-((S)-tetrahydrofuran-3-yloxy)quinazolin-6-yl)-4-(2-(hydroxymethyl)azetidin-1-yl)but-2-enamide (11)

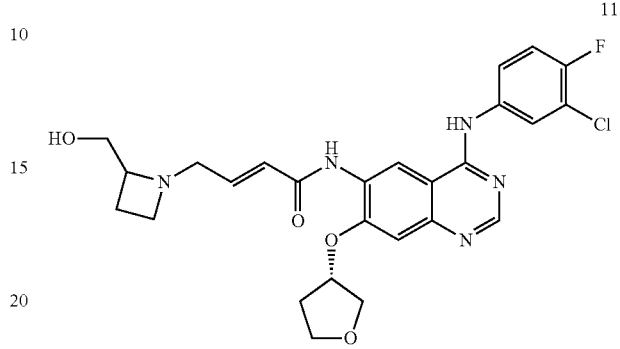

The title compound was prepared by using the same procedure as described for Example 1 by replacing intermediate A with intermediate E. MS-ESI (m/z): 528 [M+H]⁺.

Example 12

(E)-N-(4-(3-chloro-4-fluorophenylamino)-7-((S)-tetrahydrofuran-3-yloxy)quinazolin-6-yl)-4-(2-(methoxymethyl)azetidin-1-yl)but-2-enamide (12)

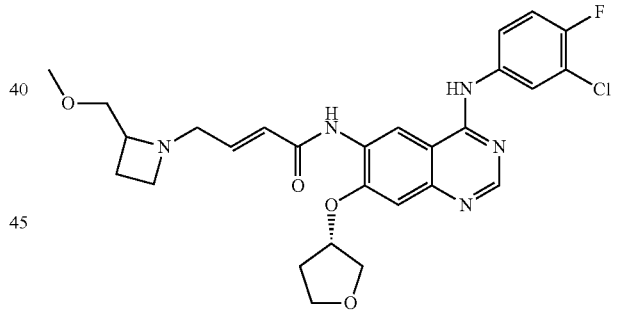

benzyl 1-benzylazetidine-2-carboxylate (12a)

A mixture of benzyl 2,4-dibromobutanoate (8.50 g, 25.2 mmol), benzylamine (4.05 g, 37.8 mmol) and K$_2$CO$_3$ (8.70 g, 63.1 mmol) in Acetonitrile (70 mL) was heated to 85° C. overnight. The mixture was cooled to room temperature and filtered. The cake was washed with EtOAc (30 mL). The combined filtrate was concentrated under reduced pressure. The residue was purified by column chromatography on silica gel eluting with PE/EtOAc (20:1~10:1) to give the title compound 12a (4.0 g) as yellow oil. MS-ESI (m/z): 282.0 [M+1]$^+$.

1-(tert-butoxycarbonyl)azetidine-2-carboxylic acid (12b)

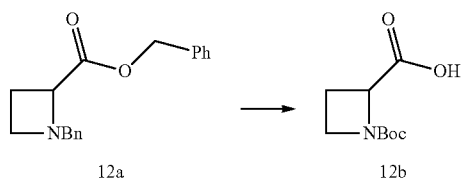 [SMILES: O=C(OCc1ccccc1)C1CCN1Cc1ccccc1 ; CC(C)(C)OC(=O)N1CCC1C(=O)O]

A mixture of 12a (3.70 g, 13.2 mmol), Di-tert butyl dicarbonate (5.70 g, 26.3 mmol), and Pd(OH)$_2$ (0.90 g, 6.43 mmol) in MeOH (100 mL) was stirred under H$_2$ atmosphere at 50° C. for 7 hours. The reaction mixture was cooled to room temperature and filtered. The filtrate was treated with 2 N NaOH (40 mL) and stirred at room temperature overnight. The reaction mixture was concentrated under reduced pressure. The residue was extracted with EtOAc (50 mL). The liquid phase was acified with 1 N HCl, adjusted pH=2 and extracted with DCM:i-PrOH=4:1 (150 mL×3). The combined organic layers was washed with water (100 mL), dried over Na$_2$SO$_4$ and concentrated under reduced pressure to give the title compound 12b (2.50 g) as colorless oil. MS-ESI (m/z): 146.0 [M+1−56]$^+$.

tert-butyl 2-(hydroxymethyl)azetidine-1-carboxylate (12c)

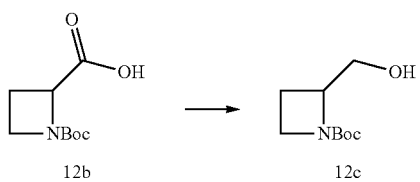 [SMILES: CC(C)(C)OC(=O)N1CCC1C(=O)O ; CC(C)(C)OC(=O)N1CCC1CO]

To a solution of 12b (1.45 g, 7.21 mmol) in anhydrous THF (12 mL) was added dropwise Borane-methyl sulfide complex (10M, 3 mL) at 0° C. The reaction mixture was warmed to room temperature for 3 hours. Then it was quenched with MeOH (10 mL), diluted with DCM (100 mL), washed with water (40 mL×3), dried over Na$_2$SO$_4$ and concentrated under reduced pressure to give the title compound 12c (1.25 g) as colorless oil. MS-ESI (m/z): 132.0 [M+1−56]$^+$.

2-(methoxymethyl)azetidine trifluoroacetic acid salt (12d)

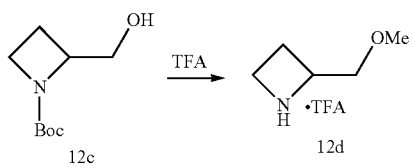 [SMILES: CC(C)(C)OC(=O)N1CCC1CO ; COCC1CCN1]

The title compound was prepared by using the same procedure as described for 2c by replacing 2b with 12c. MS-ESI (m/z): 102 [M+H]$^+$.

(E)-N-(4-(3-chloro-4-fluorophenylamino)-7-((S)-tetrahydrofuran-3-yloxy)quinazolin-6-yl)-4-(2-(methoxymethyl)azetidin-1-yl)but-2-enamide (12)

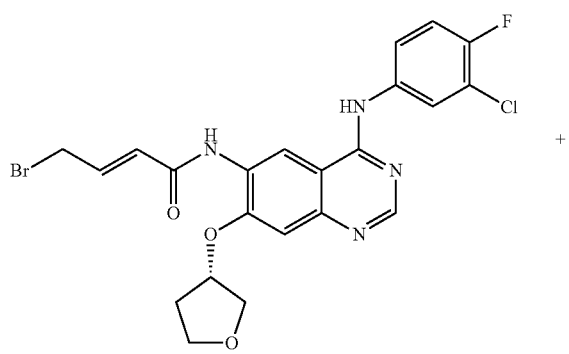

Intermediate E

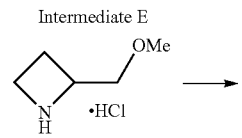

12d

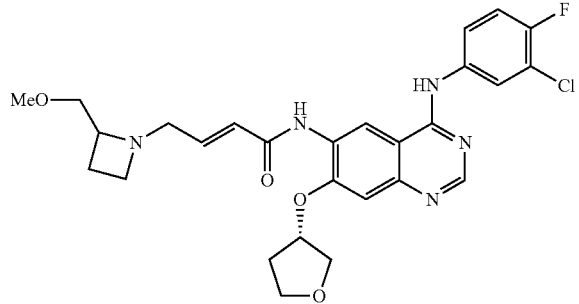

12

The title compound was prepared by using the same procedure as described for Example 1 prepared from intermediate E and 12d. MS-ESI (m/z): 542 [M+H]$^+$.

Example 13

(E)-N-(7-(((R)-1,4-dioxan-2-yl)methoxy)-4-(3-chloro-4-fluorophenylamino) quinazolin-6-yl)-4-(2-(hydroxymethyl)azetidin-1-yl)but-2-enamide (13)

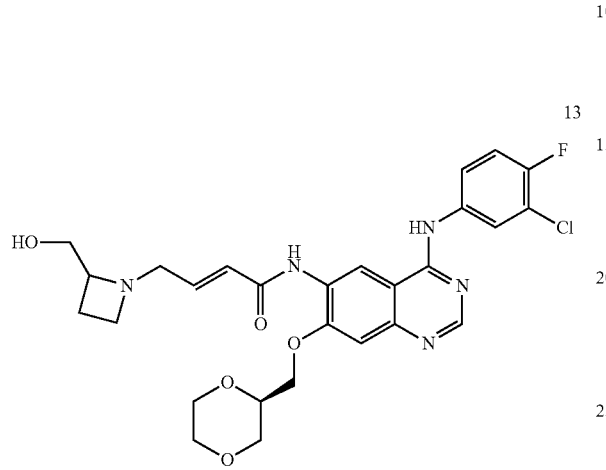

The title compound was prepared by using the same procedure as described for Example 1 by replacing intermediate A with intermediate F. MS-ESI (m/z): 558 [M+H]$^+$.

Example 14

(E)-N-(7-(((R)-1,4-dioxan-2-yl)methoxy)-4-(3-chloro-4-fluorophenylamino) quinazolin-6-yl)-4-((R)-2-(methoxymethyl)azetidin-1-yl)but-2-enamide (14)

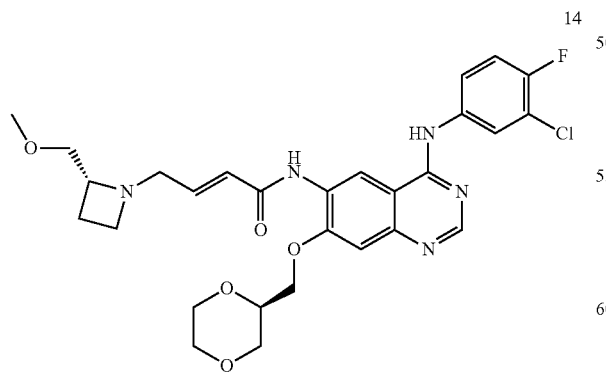

The title compound was prepared by using the same procedure as described for Example 2 by replacing intermediate A with intermediate F. MS-ESI (m/z): 572 [M+H]$^+$.

Example 15

(E)-N-(7-(((R)-1,4-dioxan-2-yl)methoxy)-4-(3-chloro-4-fluorophenylamino) quinazolin-6-yl)-4-((S)-2-(methoxymethyl)azetidin-1-yl)but-2-enamide (15)

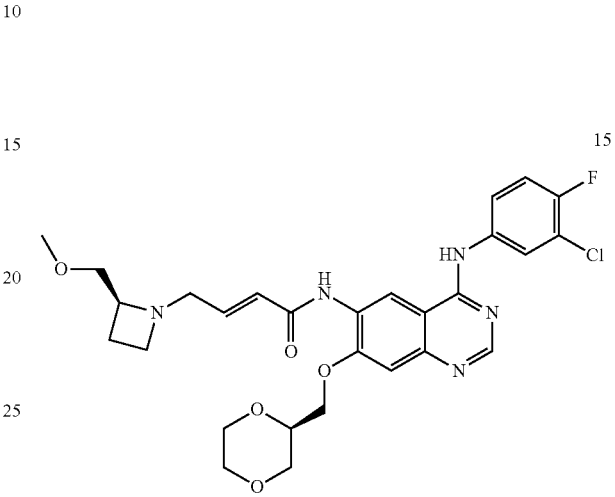

The title compound was prepared by using the same procedure as described for Example 3 by replacing intermediate A with intermediate F. MS-ESI (m/z): 572 [M+H]$^+$.

Example 16

(E)-N-(7-(((S)-1,4-dioxan-2-yl)methoxy)-4-(3-chloro-4-fluorophenylamino) quinazolin-6-yl)-4-(2-(hydroxymethyl)azetidin-1-yl)but-2-enamide (16)

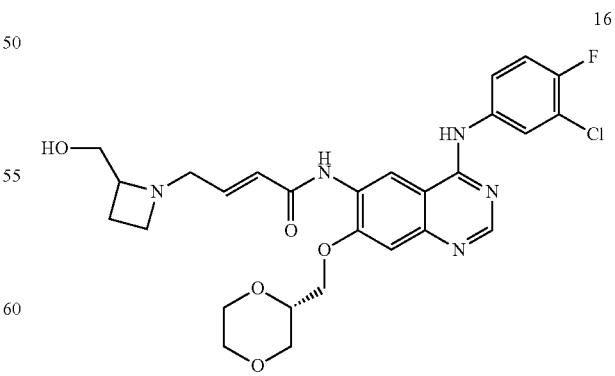

The title compound was prepared by using the same procedure as described for Example 1 by replacing intermediate A with intermediate G. MS-ESI (m/z): 558 [M+H]$^+$.

Example 17

(E)-N-(7-(((S)-1,4-dioxan-2-yl)methoxy)-4-(3-chloro-4-fluorophenylamino) quinazolin-6-yl)-4-(2-(methoxymethyl)azetidin-1-yl)but-2-enamide (17)

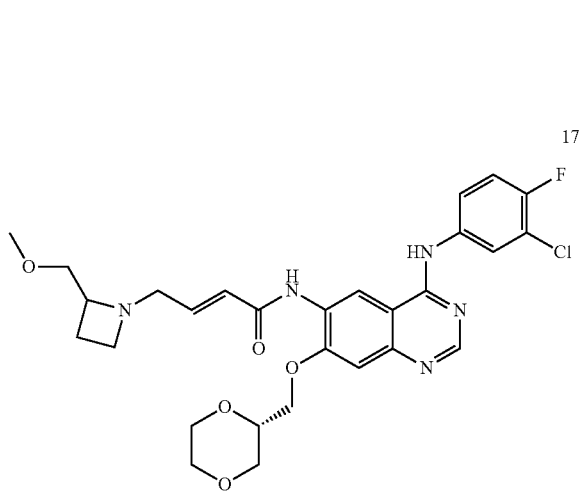 [SMILES: COCC1CCN1C/C=C/C(=O)Nc1cc2c(Nc3ccc(F)c(Cl)c3)ncnc2cc1OC[C@@H]1COCCO1]

The title compound was prepared by using the same procedure as described for Example 12 by replacing intermediate E with intermediate G. MS-ESI (m/z): 572 [M+H]$^+$.

Example 18

(E)-N-(7-((1R,5S,6r)-3-oxabicyclo[3.1.0]hexan-6-ylmethoxy)-4-(3-chloro-4-fluorophenylamino)quinazolin-6-yl)-4-(2-(hydroxymethyl)azetidin-1-yl)but-2-enamide (18)

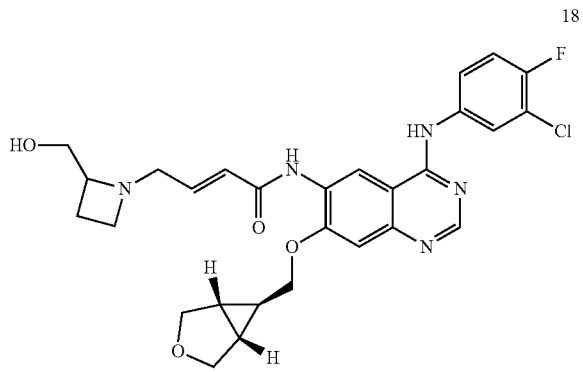 [SMILES: COC[C@H]1CCN1C/C=C/C(=O)Nc1cc2c(Nc3ccc(F)c(Cl)c3)ncnc2cc1OC[C@H]1[C@@H]2COC[C@@H]21]

The title compound was prepared by using the same procedure as described for Example 1 by replacing intermediate A with intermediate H. MS-ESI (m/z): 554 [M+H]$^+$.

Example 19

(E)-N-(7-((1R,5S,6r)-3-oxabicyclo[3.1.0]hexan-6-ylmethoxy)-4-(3-chloro-4-fluorophenylamino)quinazolin-6-yl)-4-((R)-2-(methoxymethyl)azetidin-1-yl)but-2-enamide (19)

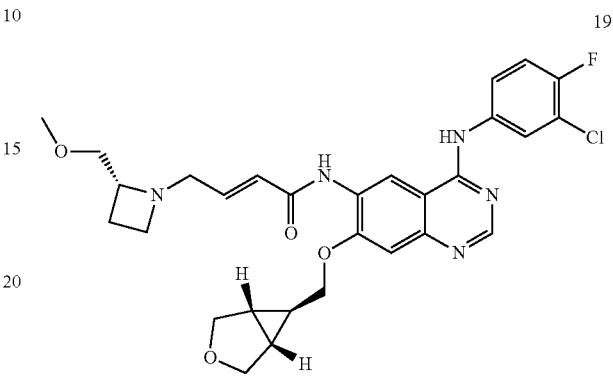

The title compound was prepared by using the same procedure as described for Example 2 by replacing intermediate A with intermediate H. MS-ESI (m/z): 568 [M+H]$^+$.

Example 20

(E)-N-(7-((1R,5S,6r)-3-oxabicyclo[3.1.0]hexan-6-ylmethoxy)-4-(3-chloro-4-fluorophenylamino)quinazolin-6-yl)-4-((S)-2-(methoxymethyl)azetidin-1-yl)but-2-enamide (20)

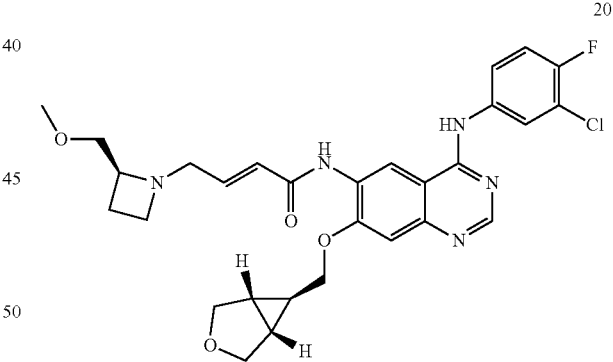

The title compound was prepared by using the same procedure as described for Example 3 by replacing intermediate A with intermediate H. MS-ESI (m/z): 568 [M+H]$^+$.

Cell Proliferation Asssay

Materials and Preparation of Reagents

MTS testing kit was purchased from Promega. The RPMI-1640, DMEM, Fetal bovine serum and Penicillin-Streptomycin were purchased from Gibco. Dimethyl sulfoxide (DMSO) was purchased from Sigma.

Inhibition Activity of Cell Proliferation

To investigate whether a compound is able to inhibit the activity of EGFR and ErbB2 in cells, a mechanism-based assay using BT474 (EGFR overexpression) and N87 (EGFR and ErbB2 overexpression) cell was developed. In this assay, inhibition of EGFR and ErbB2 was detected by the inhibition of BT474 and N87 cells proliferation. BT474 cells were cultured in culture flasks to 40-80% confluence in DMEM plus 10% fetal bovine serum. N87 cells were cultured in culture flasks to 40-80% confluence in RPMI-1640 plus 10% fetal bovine serum. Cells were collected and plated onto 96-well plates at desired cell density (BT474: 1000 cells/well; N87: 1000 cells/well). BT474 plates were incubated 48 h at 37° C., with 5% $CO_2$ to adhere. N87 plates were incubated overnight at 37° C., with 5% $CO_2$ to adhere. Compounds were added to the plates, The final compound concentrations were 1000, 333.3, 111.1, 27.04, 12.35, 4.12, 1.37, 0.46 and 0.15 nM. Place BT474 plates at 37° C., with 5% $CO_2$ for 7d. Place N87 plates at 37° C., with 5% $CO_2$ for 72 h. After removing the medium, 20 μl MTS/100 μl medium mixture solution were added to each well and incubate the plates for exactly 2 hours. Measure absorbance at 490 nm and 650 nm (reference wavelength). $IC_{50}$ was calculated using GraphPad Prism 5.0.

Select compounds prepared as described above were assayed according to the biological procedures described herein. The results are given in the table 1.

TABLE 1

| EXAMPLE | NAME | BT474 $IC_{50}$ (nM) | N87 $IC_{50}$ (nM) |
|---|---|---|---|
| 1 | (E)-N-(4-(3-chloro-4-fluorophenylamino)-7-methoxyquinazolin-6-yl)-4-(2-(hydroxymethyl)azetidin-1-yl)but-2-enamide | 2.3 | 5.0 |
| 2 | (R,E)-N-(4-(3-chloro-4-fluorophenylamino)-7-methoxyquinazolin-6-yl)-4-(2-(methoxymethyl)azetidin-1-yl)but-2-enamide | 1.6 | 1.6 |
| 3 | (S,E)-N-(4-(3-chloro-4-fluorophenylamino)-7-methoxyquinazolin-6-yl)-4-(2-(methoxymethyl)azetidin-1-yl)but-2-enamide | 21.5 | 14.2 |
| 4 | (R,E)-N-(4-(3-chloro-4-fluorophenylamino)-7-ethoxyquinazolin-6-yl)-4-(2-(methoxymethyl)azetidin-1-yl)but-2-enamide | 2.0 | 1.6 |
| 5 | (S,E)-N-(4-(3-chloro-4-fluorophenylamino)-7-ethoxyquinazolin-6-yl)-4-(2-(methoxymethyl)azetidin-1-yl)but-2-enamide | 7.8 | 8.1 |
| 6 | (R,E)-N-(4-(3-chloro-4-fluorophenylamino)-7-(2-methoxyethoxy)quinazolin-6-yl)-4-(2-(methoxymethyl)azetidin-1-yl)but-2-enamide | 1.4 | 1.9 |
| 7 | (S,E)-N-(4-(3-chloro-4-fluorophenylamino)-7-(2-methoxyethoxy)quinazolin-6-yl)-4-(2-(methoxymethyl)azetidin-1-yl)but-2-enamide | 5.8 | 4.6 |
| 8 | (E)-N-(4-(3-chloro-4-fluorophenylamino)-7-(cyclopropylmethoxy)quinazolin-6-yl)-4-(2-(hydroxymethyl)azetidin-1-yl)but-2-enamide | 9.5 | 11.8 |
| 9 | (R,E)-N-(4-(3-chloro-4-fluorophenylamino)-7-(cyclopropylmethoxy)quinazolin-6-yl)-4-(2-(methoxymethyl)azetidin-1-yl)but-2-enamide | 6.6 | 15.5 |
| 10 | (S,E)-N-(4-(3-chloro-4-fluorophenylamino)-7-(cyclopropylmethoxy)quinazolin-6-yl)-4-(2-(methoxymethyl)azetidin-1-yl)but-2-enamide | 21.7 | 32.8 |
| 11 | (E)-N-(4-(3-chloro-4-fluorophenylamino)-7-((S)-tetrahydrofuran-3-yloxy)quinazolin-6-yl)-4-(2-(hydroxymethyl)azetidin-1-yl)but-2-enamide | 3.9 | 9.6 |
| 12 | (E)-N-(4-(3-chloro-4-fluorophenylamino)-7-((S)-tetrahydrofuran-3-yloxy)quinazolin-6-yl)-4-(2-(methoxymethyl)azetidin-1-yl)but-2-enamide | 2.9 | 1.5 |
| 13 | (E)-N-(7-(((R)-1,4-dioxan-2-yl)methoxy)-4-(3-chloro-4-fluorophenylamino)quinazolin-6-yl)-4-(2-(hydroxymethyl)azetidin-1-yl)but-2-enamide | 2.7 | 13.5 |
| 14 | (E)-N-(7-(((R)-1,4-dioxan-2-yl)methoxy)-4-(3-chloro-4-fluorophenylamino)quinazolin-6-yl)-4-((R)-2-(methoxymethyl)azetidin-1-yl)but-2-enamide | 2.9 | 1.2 |
| 15 | (E)-N-(7-(((R)-1,4-dioxan-2-yl)methoxy)-4-(3-chloro-4-fluorophenylamino)quinazolin-6-yl)-4-((S)-2-(methoxymethyl)azetidin-1-yl)but-2-enamide | 25.0 | 11.2 |
| 16 | (E)-N-(7-(((S)-1,4-dioxan-2-yl)methoxy)-4-(3-chloro-4-fluorophenylamino)quinazolin-6-yl)-4-(2-(hydroxymethyl)azetidin-1-yl)but-2-enamide | 17.5 | 39.5 |
| 17 | (E)-N-(7-(((S)-1,4-dioxan-2-yl)methoxy)-4-(3-chloro-4-fluorophenylamino)quinazolin-6-yl)-4-(2-(methoxymethyl)azetidin-1-yl)but-2-enamide | 4.8 | 5.0 |
| 18 | (E)-N-(7-((1R,5S,6R)-3-oxabicyclo[3.1.0]hexan-6-ylmethoxy)-4-(3-chloro-4-fluorophenylamino)quinazolin-6-yl)-4-(2-(hydroxymethyl)azetidin-1-yl)but-2-enamide | 10.8 | 11.2 |
| 19 | (E)-N-(7-((1R,5S,6R)-3-oxabicyclo[3.1.0]hexan-6-ylmethoxy)-4-(3-chloro-4-fluorophenylamino)quinazolin-6-yl)-4-((R)-2-(methoxymethyl)azetidin-1-yl)but-2-enamide | 2.9 | 2.8 |

TABLE 1-continued

| EXAMPLE | NAME | BT474 IC$_{50}$ (nM) | N87 IC$_{50}$ (nM) |
|---|---|---|---|
| 20 | (E)-N-(7-((1R,5S,6R)-3-oxabicyclo[3.1.0]hexan-6-ylmethoxy)-4-(3-chloro-4-fluorophenylamino)quinazolin-6-yl)-4-((S)-2-(methoxymethyl)azetidin-1-yl)but-2-enamide | 22.2 | 15.6 |

N87 Tumor In Vivo Study

Female BALB/cA-nude mice were implanted with NCI-N87 tumor cells. Tumor measurements were recorded twice a week. Randomize animals to groups (Day 0) when tumors reached an average size of 60-150 mm$^3$. Group size was 6 mice. Test compound was administered p.o. once daily for 21 days. Tumor inhibition values were determined at Day 21.

Tumor inhibition for provided compounds were shown in FIG. 1 and Table 2. Tumor volume (V) was calculated as follow: V=½×a×b, where a and b are the length and width of the tumor respectively. Relative tumor proliferation rate was calculated as follow: T/C (%)=(T−T$_0$)/(C−C$_0$)×100, where T and C are the tumor volume of test compound group and control group on Day 21, T$_0$ and C$_0$ are the tumor volume of test compound group and control group on Day 0.

TABLE 2

Tumor inhibition of test compounds

| Example | Dosage (mg/kg) | Average Tumor Volume (mm$^3$) Day 0 | Average Tumor Volume (mm$^3$) Day 21 | T/C (%) | Inhibition rate (%) |
|---|---|---|---|---|---|
| Vehicle Control | — | 115.0 ± 3.6 | 1324.8 ± 122.5 | — | — |
| 2 | 2 | 113.3 ± 4.4 | 584.4 ± 71.3 | 39 | 61 |
| 2 | 5 | 117.6 ± 7.2 | 54.3 ± 3.8 | −54 | 154 |
| 4 | 2 | 105.6 ± 9.9 | 436.6 ± 60.5 | 27 | 73 |
| 4 | 5 | 109.1 ± 10.1 | 49.7 ± 5.4 | −54 | 154 |
| 6 | 5 | 116.9 ± 7.8 | 176.3 ± 24.2 | 5 | 95 |
| 6 | 10 | 114.8 ± 7.8 | 49.0 ± 3.9 | −57 | 157 |
| 9 | 5 | 124.1 ± 8.5 | 349.3 ± 43.8 | 19 | 81 |
| 9 | 10 | 120.2 ± 13.0 | 60.3 ± 6.9 | −50 | 150 |
| Afatinib | 20 | 117.2 ± 8.3 | 72.9 ± 7.9 | −38 | 138 |
| Lapatinib | 320 | 124.4 ± 7.3 | 277.3 ± 74.1 | 13 | 87 |

What is claimed is:

1. A compound, wherein the compound is;
(R,E)-N-(4-(3-chloro-4-fluorophenylamino)-7-ethoxy-quinazolin-6-yl)-4-(2-(methoxymethyl)azetidin-1-yl)but-2-enamide
or a pharmaceutically acceptable salt thereof.

2. A pharmaceutical composition, comprising the compound of claim 1, or a pharmaceutically acceptable salt thereof, and at least one pharmaceutically acceptable carrier.

* * * * *